United States Patent [19]
Sievers et al.

[11] Patent Number: 5,941,813
[45] Date of Patent: Aug. 24, 1999

[54] CARDIAC ASSIST DEVICE

[75] Inventors: Hans-Hinrich Sievers, Kronshagen; Wolfgang Kloess, Lubeck; Wolfgang Daum, Schwerin, all of Germany

[73] Assignee: Cardiotools Herzchirurgietechnik Gmbh, Schwerin, Germany

[21] Appl. No.: 08/898,302

[22] Filed: Jul. 22, 1997

[30] Foreign Application Priority Data

Jul. 23, 1996 [DE] Germany .......................... 196 29 614

[51] Int. Cl.$^6$ ................................................ A61M 1/10
[52] U.S. Cl. ............................................................ 600/16
[58] Field of Search ................................. 600/16, 17, 18

[56] References Cited

U.S. PATENT DOCUMENTS

| | | | |
|---|---|---|---|
| 4,944,748 | 7/1990 | Bramm et al. . | |
| 4,957,504 | 9/1990 | Chardack | 600/16 |
| 5,578,012 | 11/1996 | Kamen et al. | 600/16 |
| 5,613,935 | 3/1997 | Jarvik | 600/16 |

OTHER PUBLICATIONS

Harbott, et al., "Rotary blood pumps in circulatory assist," *Perfusion*, 10:153–158 (1995).

Mussivand, et al., "Totally Implantable Intrathoracic Ventricular Assist Device," *Ann Thorac Surg*, 61:444–447 (1996).

Guldner, et al., "First Clinical Application of the MEDOS–HIA Ventricular Support System: Monitoring of the Thrombotic Risk by means of the Biomarker Prothrombin Fragment $F_{1+2}$ and Scanning Electron Microscopy Evaluation," *J. Heart Lung Transplant.*, 15:291–296 (Mar. 1996).

Westaby, et al., "Less Invasive Coronary Surgery: Consensus From the Oxford Meeting," *Ann Thorac Surg*, 62:924–931 (1996).

*Primary Examiner*—Scott M. Getzow
*Attorney, Agent, or Firm*—Merchant, Gould, Smith, Edell, Welter & Schimdt, P.A.

[57] ABSTRACT

In a cardiac assist device, a housing has an inlet and outlet connectable to a patient's cardiovascular system. A pump is located within the housing to force blood that has entered through the inlet out through the outlet. The pump is connectable between the patient's left atrium and the aorta so as to assist the function of the left ventricle. A motor unit is also disposed within the housing, hermetically sealed from the pump. The whole unit is wholly implantable in a patient's chest. Permanently sealable valves, disposed in the inlet and outlet, may be closed without any invasive procedure to isolate the device from the heart once cardiac function assist is no longer required. The device may remain implanted within the patient indefinitely after the valves have been closed, and there is no requirement for a surgical procedure to remove the device once it is de-activated.

16 Claims, 4 Drawing Sheets

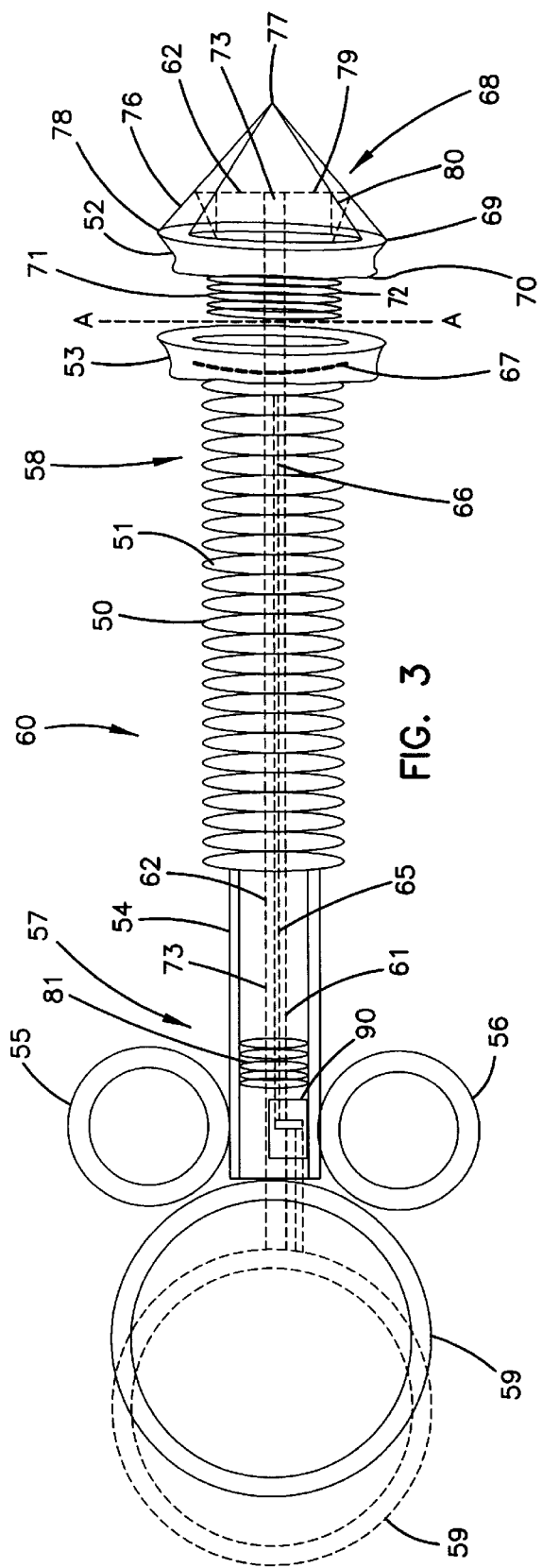

CARDIAC ASSIST DEVICE

This application is related to German patent application number 19629614.5-35, which is incorporated herein by reference.

BACKGROUND OF THE INVENTION

The invention relates to a device for assisting the cardiac function, and particularly to a device that assists the heart to pump blood when the heart is in a weakened state.

When a patient is suffering from a cardiac dysfunction, for example a disease such as dilatory cardiomyopathy, or an infection causing myocarditis, or is recovering from cardiac surgery, it is common practice to connect the patient to an external system that assists the ventricular function. Typically, these systems remove blood from the patient's pulmonary vein or left atrium through a tube, direct the blood to an external pump, and then return the blood, now at a higher pressure, to the patient's aorta. The heart assist system therefore reduces the amount of blood that the left ventricle is required to pump through the patient's body, thus reducing the load on the left heart to permit the heart's recovery.

Since such heart assist systems are external to the patient, there are several problems and disadvantages. The heart assist system is generally bulky, and has to be transported along with the patient whenever the patient is moved. Therefore, the patient is usually immobile when attached to the heart assist system. The heart assist system uses an external pump with flexible tubes inserted through the skin and into the heart and the aorta: the points at which these tubes enter the patient's body are possible centers of infection. There may also be problems of bleeding where conventional tubes are connected with the left heart and aorta due to relative motion between the anastomosis and point of entry on the patient's skin.

If the patient is attached to an external heart assist system for a long time, there is a risk of myocardial atrophy. Moreover, when it is time to remove the patient from the heart assist system, a second surgical procedure is necessary to remove the tubes inserted into the heart.

A recently developed heart assist device includes a pump that is placed within the patient's left ventricle using a catheter passing through the femoral artery. The pump is rotated by a wire passing within the catheter which is attached to a an external motor. However, since the catheter passes through the aortic valve, the valve is unable to close completely while the pump is in place. Additionally, the patient has to remain stationary while the pump is in position because of the rigid wire passing through the catheter. This requires the patient to be heavily sedated throughout the time the pump is in place. Typically such a pump remains within the patient for 2–7 hours, but may be used for up to 48 hours before the pump's efficacy is reduced due to use.

Thus, the choices faced by doctors and patients currently require that the patient either be heavily sedated during the period of use of the heart assist system, or that the patient undergo two surgical procedures, a first to implant the system and a second to extract the system after use so that the patient may regain mobility. Further, since the patient's mobility is impaired by all conventional heart assist devices, the doctor may be faced with the dilemma of taking a patient off the heart assist device before recovering full cardiac function in order to allow the patient to be mobile. This may be a particular problem when the patient's cardiac function takes several days or more to recover.

Therefore, there is a need to develop a heart assist device that avoids such a dilemma, and permits the patient to be mobile even when the device is in use. Also, there is a need to develop a heart assist device that reduces the chance of infection and which requires neither that the patient be heavily sedated during use, nor that the external device be removed after use by a surgical procedure.

SUMMARY OF THE INVENTION

In order to reduce the problems described above, one particular embodiment of a cardiac assist device includes a hermetically sealed housing having an inlet and outlet connectable to a patient's cardiovascular system. A pump located within the housing forces blood that has entered through the inlet out through the outlet. The pump is connectable between the patient's left atrium and the aorta so as to assist the function of the left ventricle. A motor unit is also disposed within the housing to drive the pump. The motor unit includes control electronics and is couplable to a power supply. Permanently sealable valves are disposed in the inlet and outlet.

In another embodiment of the cardiac assist device, a hermetically sealed pump unit has an inlet and outlet connectable to a patient's cardiovascular system. A rotor portion within the pump unit is rotatable to force blood entering the pump unit through the inlet out through the outlet. The device also includes a hermetically sealed motor unit including control electronics and stator windings to produce a magnetic field couplable to the rotor portion. The motor unit is couplable to a power supply.

The present invention also provides a prosthesis placement system for attaching a cardiac assist device to a patient's cardiovascular system.

The above summary of the present invention is not intended to describe each embodiment or every implementation of the present invention. The FIGs. and the detailed description which follow exemplify particular embodiments within the scope of the invention.

BRIEF DESCRIPTION OF THE DRAWINGS

The invention may be more completely understood in consideration of the following detailed description of various embodiments of the invention in connection with the accompanying drawings in which:

FIG. 3 illustrates a prosthesis placement system (PPS) for connecting the implantable cardiac assist device and the heart;

FIG. 4 illustrates an enlargement of a portion of a proximal locking ring advancement mechanism (PLRAM) of the prosthesis placement system (PPS) of FIG. 3;

FIG. 5 illustrates a cross section of the prosthesis placement system (PPS) of FIG. 3 at line A—A distal to the proximal locking ring and advancing member.

Figure 1:
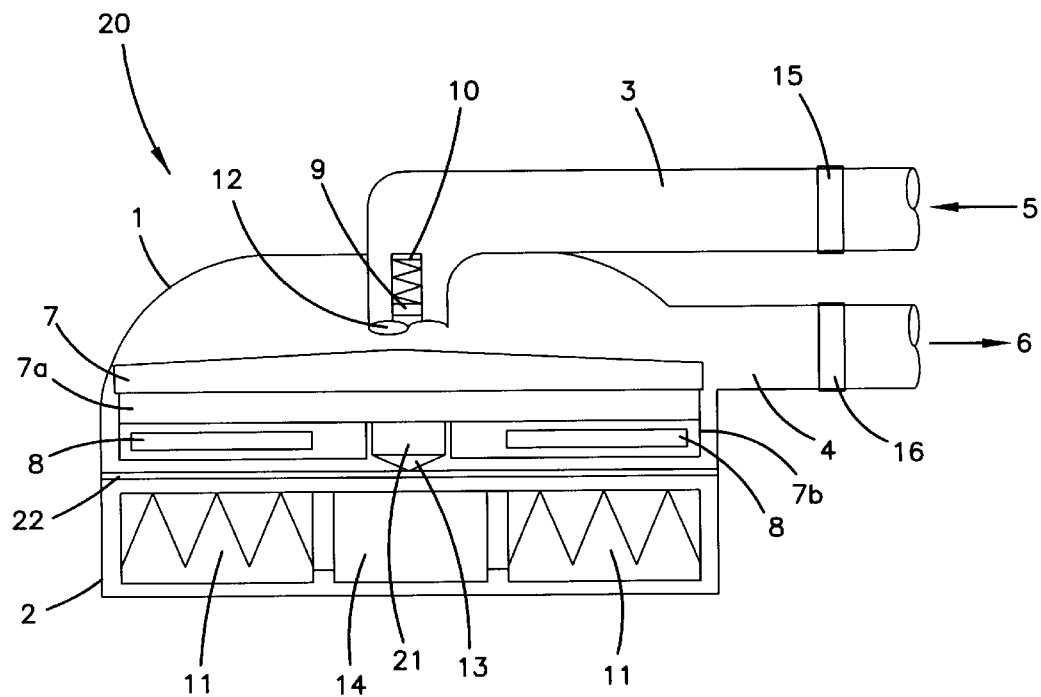
FIG. 1 illustrates a cross-section of a first embodiment of an implantable cardiac assist device.

While the invention is amenable to various modifications and alternative forms, specifics thereof have been shown by way of example in the drawings and will be described in detail. However, it should be understood that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is an implantable cardiac assist device, including that disclosed in the related German Patent Application No. 19629614.5-35, from which priority is claimed. The implantable cardiac assist device may have no external connections, and so the patient does not need to remain immobilized while using the assist device, thus permitting faster recovery. Also, where there are no external connections, the risk of infection is greatly reduced. Once the heart has recovered to the point where the assist device is no longer needed, the device may be deactivated and physically isolated from the heart by valves without opening the patient's chest. Thus, the device may remain implanted within the patient even after it is no longer in use. An implantable device does not require the use of tubes passing through the patient's skin, thus reducing the risk of infection Moreover, the risk of bleeding at the anastomosis is reduced, since there is no external part to cause large movements.

The cardiac assist device is especially suited to assist the myocardial function by supplementing the operation of the left ventricle. Accordingly, the following description is directed to a situation where the cardiac assist device supplements the operation of the left ventricle.

One particular embodiment of the cardiac assist device is illustrated in FIG. 1. This embodiment is described in German Patent Application No. 19629614.5-35, which is incorporated herein by reference. The device 20 includes a pump unit 1 that is hermetically sealed from the motor unit 2. The pump unit 1 is hermetically sealed except for an inlet 3 receiving blood from the left atrium and an outlet 4 to allow blood to be pumped into the aorta. In this embodiment, the pump 1 includes a rotor 7a mounted on a shaft 21 between on a first cone-shaped bearing 12 and a second cone-shaped bearing 13. The first bearing 12 may be coupled to a sprung piston 10 in a cylinder 9 in order to reduce the effect of abrasion and wear on the bearings 12 and 13. Thus, the bearings 12 and 13 maintain constant contact with their appropriate bearing surfaces even when the bearings 12 and 13 wear down.

The rotor 7a includes an integral impeller 7 and a number of permanent magnets 8 disposed around an integral lower portion 7b. The impeller 7 may be formed from a rubber-like material, or a biologically compatible pseudo-elastic material such as nickel-titanium. Blood from the inlet 3 is directed to the center portion of the impeller 7. Rotation of the impeller 7 directs the blood out through the outlet 4 at a higher pressure than at the inlet 3. The pump rate of the impeller 7 may be controlled by the control electronics 14 according to the demand on the heart. For example, the impeller speed may be increased when the heart rate increases.

Typically, the cardiac assist device 20 assists in left ventricle output. The pump rate of the device 20 is selected to compensate for any ventricular deficiency by setting an appropriate impeller rotation rate. If at any time the blood pressure at the outlet 4 is higher than the pressure of the blood in the left ventricle, the patient's aortic valve prevents the backward flow of blood from the aorta into the left ventricle.

The motor unit 2, hermetically isolated from the pump unit 1, includes control electronics 14 that are connected to stator windings 11. The control electronics 14 are connected to an electrical power supply (not shown), for example a battery. The power supply may be implanted in the patient, either within or outside the cardiac assist device 20, or it may be maintained external to the patient, for example attached to the device 20 via leads passing through the patient's skin, or coupled inductively to the control electronics 14. When the power supply is external, it may take the form of a battery pack that is strapped on the patient so that the patient's mobility is not impaired.

Conventional pump motors used in heart assist devices include synchronous, asynchronous and step motors. In these case, the rotor shaft is used to move pump components which are external to the motor. This requires a dynamic seal on the motor shaft, which may degrade under use. Thus, an important feature of the presently claimed invention is that the rotor 7a is contained within a hermetically sealed pump housing 1, thus avoiding problems associated with a dynamic seal on the motor shaft.

The control electronics 14 control the current flowing through the stator windings 11 so as to create a rotating magnetic field that couples to the permanent magnets 8 through the walls of the pump unit 1 and the motor unit 2. Thus, the rotor 7a rotates synchronously with the rotating magnetic field created by the stator windings 11. A change in the rotation rate of the rotating magnetic field results in a corresponding change in the rotation rate of the rotor 7a. The air gap between the rotor 7a and the stator windings 11 is defined by the material thickness of the wall 22 between the pump unit and the motor unit.

Valves 15 and 16 are provided on the inlet 3 and the output 4 from the pump 1. In one particular embodiment, these valves 15 and 16 are formed from a biologically compatible shape memory metal, such as nickel-titanium. Shape memory metals change shape when they undergo a phase transition when, for example, they are subjected to heat. The valves 15 and 16 may be of a number of physical geometries. For example, the valves 15 and 16 may be iris-type valves that close when subjected to heat. The valves 15 and 16 may also be flap-type valves that seal against a sealing ring disposed within the respective inlet 3 and outlet 4. When activated, the shape memory valves 15 and 16 form permanent seals to isolate the pump 1 from the heart. Therefore, once a patient's heart has recovered to the point where it can operate without the cardiac assist device 20, the device 20 may be permanently isolated from the heart by closing the shape memory valves 15 and 16.

While the assist device 20 is operational, the valves 15 and 16 are open to permit flow in either direction. This is unlike many conventional heart assist devices which use one way valves. When it is desired to isolate the assist device 20 from the heart, the valves 15 and 16 are activated to close, typically by heating. Activation may take place in a number of different ways, including inductive heating by a source outside the patient's chest cavity, or heating, either inductively or resistively, by the control electronics 14.

In an operational example of the device 20, the overall device diameter is about 5 cm, and the impeller diameter is 4 cm. The impeller 7 normally rotates at approximately 3000 r.p.m., to create a pressure difference across the device 20 of approximately 100 mmHg. The impeller may rotate at speeds ranging from approximately 2500 r.p.m. to approximately 6000 r.p.m, producing pressures ranging from approximately 60 mmHg to approximately 200 mmHg.

The cardiac assist device 20 is sufficiently small that the device, including the electric motor and tube connections may be implanted in the thorax of the patient, for example behind the sternum, even if the patient is very slim. An important feature of the cardiac assist device 20 is that, because it is small and hermetically sealed, it may remain implanted in the patient for an indefinite period of time after its useful life is over and the valves 15 and 16 have been closed to isolate the device 20 from the cardiovascular system. The cardiac assist device 20 does not have to be removed when the patient's heart recovers, thus avoiding the need for a surgical operation to remove the device once it no longer in use. The cardiac assist device 20 may subsequently be removed from the patient's chest at any time, for example during any subsequent thoracic surgical procedure.

A significant difference between conventional heart assist pumps and the present invention is that the present invention does not require an external pump to circulate the blood. Instead, the present invention includes a pump and motor which are implanted in the patient's thorax and the only external component is a small power supply.

The cardiac assist device 20 has been described herein as an auxiliary pump connected in parallel across the left ventricle. Used in this way, it does not present a complete substitute for the heart, which is allowed to continue beating while the assist device is operating. Accordingly, pulsating pressure differences may arise. In order to reduce the rate of hemolysis on the impeller 7 at the pulsating pressure peaks, the impeller 7 may be formed of a resiliently deformable material, such as rubber or the like, so that the impeller 7 can yield under increased pressure, and reduce hemolysis.

Figure 2:
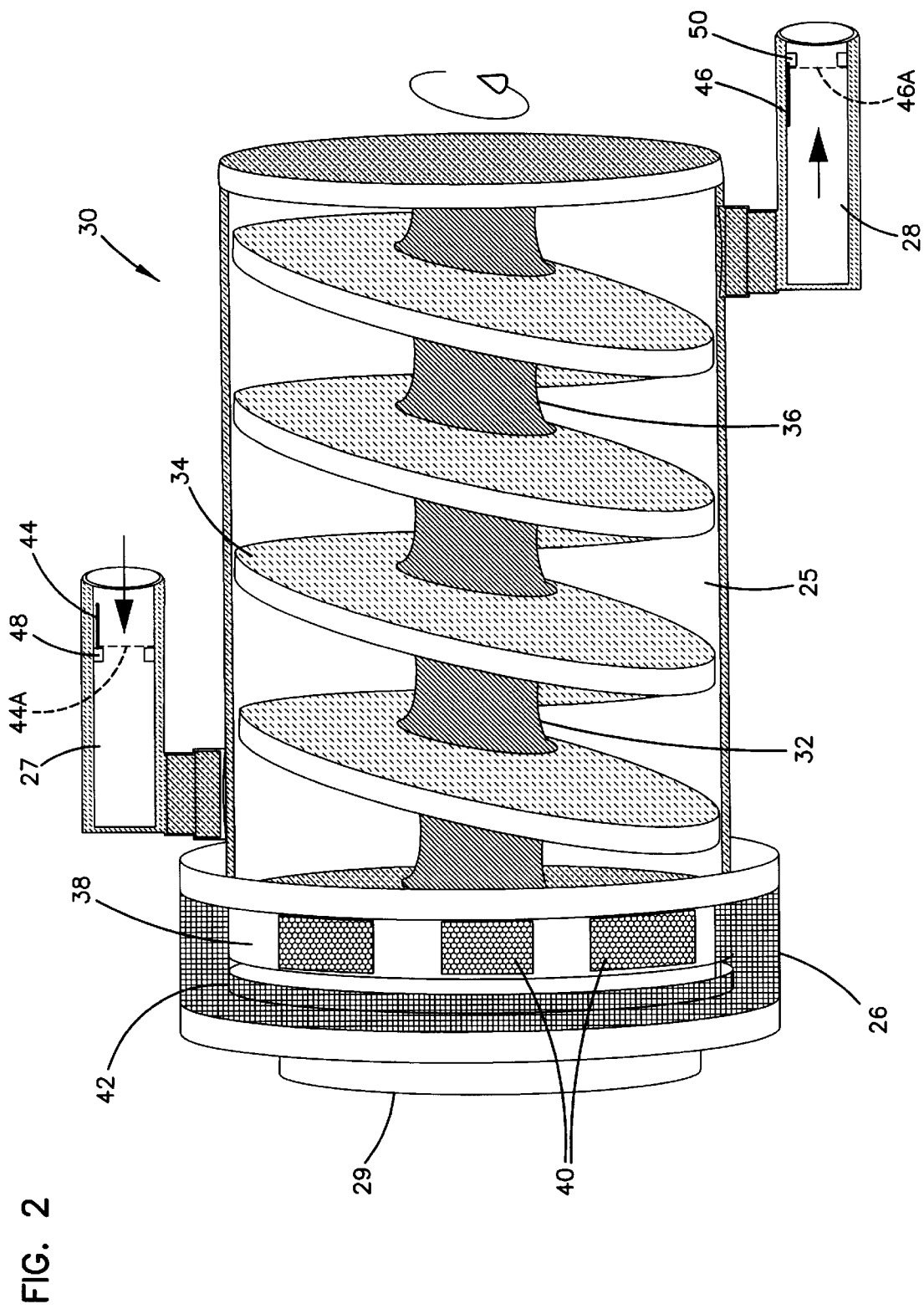
FIG. 2 illustrates a cross-section of a second embodiment of an implantable cardiac assist device.

Another embodiment of the cardiac assist device 30 is illustrated in FIG. 2. Many parts of this embodiment of the device 30 are similar to those illustrated in FIG. 1, and are identified using similar labels.

In this particular embodiment, the pump unit 25 is based on an Archimedes screw. The rotor 32 is mounted within the pump unit on rotatable bearings (not shown) holding the shaft 36. The rotor includes a screw 34 that, when rotating, forces blood entering the pump unit from the intake 27 along the length of the pump unit 25 and out through the outlet 28.

The rotor also includes a base portion 38 at the same end of the pump unit 25 as the motor unit 26. A number of permanent magnets 40 are located on the base portion 38, with their poles positioned radially with respect to the shaft 36.

The motor unit 26 is located at one end of the pump unit 25 and hermetically sealed therefrom. The motor unit 26 is shaped like a collar that fits around the end of the pump unit. When activated by the control electronics 29, the coils 42 within the motor unit 26 generate rotating magnetic fields that couple to the permanent magnets 40. Thus, the rotor 32 rotates along with the rotating magnetic field generated by the coils 42. This motor unit is different from that illustrated in FIG. 1. In FIG. 1, the rotating magnetic fields close to the coils 11 lie perpendicular to the plane of rotation. In this embodiment, the rotating magnetic fields close to the coils 42 lie parallel to the plane of rotation. It will be appreciated that both motor geometries are applicable to use with both an impeller and an Archimedes screw-type pump.

The shape memory metal valves 44 and 46 are illustrated in the inlet 27 and outlet 28 respectively as flap-type valves in open positions. Sealing rings 48 and 50 are provided within the inlet 27 and outlet 28. When the shape memory metal valves 48 and 50 are activated, they flap into a closed position, illustrated as dashed lines 44A and 46A, to seal against the sealing rings 48 and 50.

It will be appreciated that the pump rate of the screw 34 may be altered by changing its speed of rotation and also by changing the angle that the screw 34 makes with the shaft 34. This latter result arises because the volume of blood captured in the space between one turn of the screw 34 is increased if the angle is increased towards 90°, and reduced if the angle is reduced away from 90°. Thus, if the angle is varied, then the pump rate of the screw 34 alters, even if the rotation rate remains constant. Vibrations of the screw 34 may result in pulsations in the blood flowing out of the outlet 28.

In an operational example of the device 30, the overall device diameter is about 4 cm, the length is about 7 cm and the screw diameter is 3.5 cm. The screw 34 normally rotates at approximately 200 r.p.m., to create a pressure difference across the device 30 of approximately 100 mmHg. The screw 34 may rotate at speeds ranging from approximately 100 r.p.m. to approximately 300 r.p.m, producing pressures ranging from approximately 60 mmHg to approximately 200 mmHg.

Admission and discharge channels (inflow and outflow, respectively) are used to couple the inlet and outlet of a cardiac assistance device to the cardiovascular system of a patient. Flexible, biocompatible prostheses suitable for coupling the device to a patient's cardiovascular system are known. In addition, another aspect of the present invention provides a prosthesis placement system (PPS) for placement of an inflow or outflow channel into the cardiovascular system.

Figure 6:
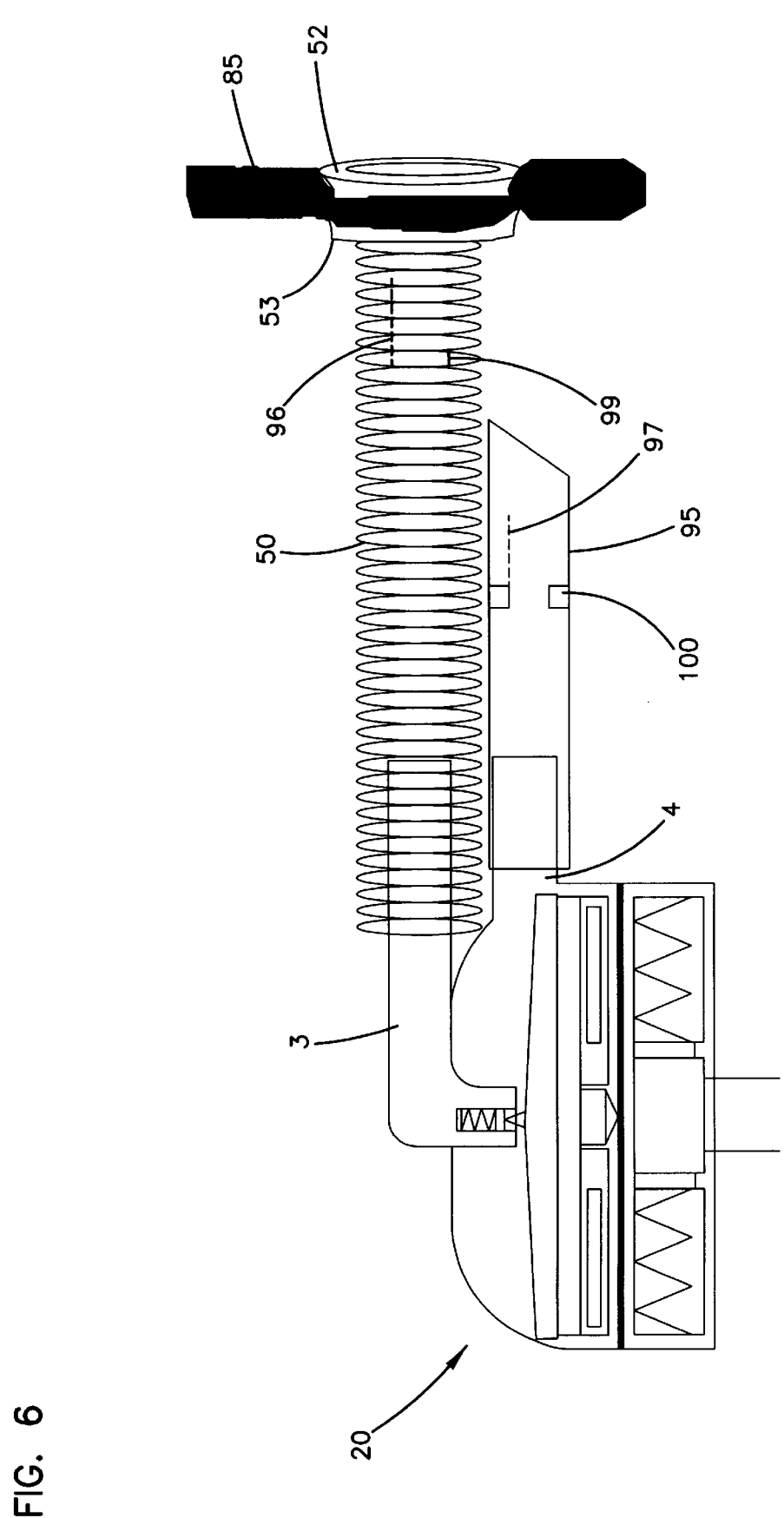
FIG. 6 illustrates the prosthesis attached to the implantable cardiac assist device of FIG. 4 and the wall of the heart.

FIGS. 3–5 illustrate an embodiment of a prosthesis placement system (PPS) particularly suited for placement of an admission (inflow) channel into the cardiovascular system, for example, into the left atrium. FIG. 6 illustrates the prosthesis in place and coupled to the inlet of a pump 20.

According to the illustrated embodiment, the PPS 60 includes an inflow channel 50 which can be prepared from a flexible biocompatible material, such as Dacron. The inflow channel 50 can include corrugations 51, at least along the internal surface of the channel, which provide for coupling to the distal locking flange 52, discussed below. The distal end of the inflow channel terminates with a proximal locking flange 53.

The PPS 60 also includes a hollow trocar 54 having two finger rings, 55 and 56, attached at the proximal end 57 of the trocar 54 for operating the PPS 60. The distal end 58 of the trocar 54 is not visible, but in the embodiment shown, the distal end 58 extends to the proximal locking flange 53. In some embodiments, the trocar is about 8 cm to 10 cm long. The PPS 60 also includes a thumb ring 59 for operating the PPS. Operably attached to and extending distally from thumb ring 59 is a proximal locking ring advancement mechanism (PLRAM) 61 and a penetrating end operating mechanism (PEOM) 62.

An enlarged view of the region of the PLRAM 61 in box 90 is shown in FIG. 4, This region of the PLRAM 61 includes a proximal shaft 63 that attaches to thumb ring 59, a reversing arm 64 and a distal arm 65. The reversing arm reverses the axial direction of travel of the distal arm 65, relative to the proximal arm 63, when the proximal arm 63 is advanced or retracted by pushing or pulling on the thumb ring 59. FIG. 5 is a cross section view taken at A—A of FIG. 3 which shows that at the distal end 66 of the distal arm 65 there is an advancing member 67 that is attached to the proximal locking flange 53. FIG. 5 shows the advancing member 67 as having 3 prongs 74a–c. Generally, at least at least two prongs are required to effectively advance the proximal locking flange 53 during use. As will be described below, when thumb ring 59 is retracted proximally (phantom 59), the reversing arm 64 of the PLRAM 61 causes the distal arm 65 to advance the advancing member 67 and proximal locking flange 53 distally. In one embodiment, rotation of thumb ring 59 causes release of prongs 74a–c from proximal locking flange 53 for removal of the PLRAM from trocar 54. The proximal locking flange 53 can include a slot 75 which allows for elastic expansion or contraction of the inside diameter of flange 53.

The PPS 60 also includes a penetrating end operating mechanism (PEOM) 62. The penetrating end 68 of the PPS is located on the distal aspect 69 of distal locking flange 52. At the proximal aspect 70 of the distal locking flange 52 is a cylindrical coupler 71 having external corrugations 72 which can interdigitate with the internal corrugations 51 of inflow channel 50. The wall of the cylindrical coupler 71 and/or the distal locking flange 52 can include a slot (not shown) which allows for elastic expansion or contraction of the outside diameter of the flange 52 or cylindrical coupler 71.

The penetrating end 68 of the PPS 61 can be made from any material which is biocompatible for a short period of time and which is structurally capable of penetrating a region of the cardiovascular system, for example the atrial wall, according to the below described procedure. Preferably, the penetrating end can be made of polyurethane, polyacetal or similar polymer. The shape of the penetrating end 68 is pyramidal having three or more, typically six to eight, supporting arms 76 extending from vertex (tip) 77 to the base 78 of the penetrating end 68. Within the penetrating end 68 is collapsible frame 79 which provides for reduction of the cross-sectional dimension of the base 78 (discussed below). The supporting arms 76 and collapsible frame can be made from any suitable material include plastics, metals such as titanium or preferably metal alloys such as nickel-titanium.

The PEOM 62 includes a shaft 73 which attaches to the thumb ring 59 at its proximal end and the collapsible frame 79 at the distal end. The collapsible frame 79 includes at least one base support member 80 for each supporting arm 76. In use, axial movement of thumb ring 59 causes shaft 73, base support members 80 and supporting arms 76 to expand and contract the base 78 of the penetrating end 68 similar to an umbrella. The PEOM also includes a biasing mechanism, such as helical spring 81, to cause distal retraction of shaft 73 when thumb ring 59 is released.

Operation of the PPS for insertion of the channel 50 into, for example the left atrial wall, is as follows. Once the patient's chest is opened, the heart is rotated to expose the left atrial wall. The PPS is grasped with a finger in each of finger rings 55 and 56 and thumb in thumb ring 59. The thumb ring 59 is advanced distally (solid lines of FIG. 3) causing the base support members 80 of the collapsible frame 79 to advance and expand the base 78 of the penetrating end 68 via separation of supporting arms 76 at base 78. The tip 77 of penetrating end 68 is inserted through the patient's left atrial wall 85 (FIG. 6). Once through the atrial wall thumb ring 59 is partially retracted to distally advance advancing member 67 and proximal locking ring 53 against distal locking ring 52 forming a seal on both sides of the atrial wall 85 (FIG. 6). The interdigitation of the external corrugations 72 of cylindrical coupler 71 with the internal corrugations 51 of inflow channel 50 secures the inflow channel 50 in place. Subsequently, thumb ring 59 is retracted further proximally to collapse collapsible frame 79 to sufficiently contract the base 78 of penetrating end 68 to permit removal of the penetrating end 68 through the proximal aspect of inflow channel 50.

The proximal end of inflow channel 50 is then attached to inlet 3 of the cardiac assist device (illustrated as 20, but it will be appreciated that the device 30 may also be used with inflow channel 50). The outlet 4 from the cardiac assist device 20 is connected to a biocompatible outflow channel 95 which is implanted into the patients aorta.

Referring to FIG. 6, instead of placing the shape memory metal valves in the inlet and outlet of the cardiac assist device, the valves 96 and 97 may be positioned in the inflow channel 50 and the outflow channel 95, respectively, so as to produce a seal positioned closer to the heart, and to reduce the amount of blood sitting in a dead space within a tube open to the cardiovascular system. The shape memory valves 96 and 97 form a seal with sealing rings 99 and 100, respectively.

While various examples were provided above, the present invention is not limited to the specifics of the examples. For example, as an alternative to the stator windings and permanent magnets illustrated in FIG. 1, the pump motor may include a circularly running coil, and a ferrometallic current carrying clamp to set the rotor in motion.

As noted above, the present invention is applicable to assisting a patient's myocardial function. Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. An implantable cardiac assist device, comprising:
   an outer housing;
   a pump unit within the housing, having an inlet and outlet connectable to a patient's cardiovascular system and having a rotor portion therein rotatable to force blood entering the pump unit through the inlet out through the outlet;
   a motor unit within the outer housing and hermetically sealed from the pump unit, the motor unit including control electronics and windings to produce a magnetic field couplable to the rotor portion, the motor unit being couplable to a power supply; and
   shape memory valves disposed in the inlet and outlet, actuatable so as to permanently seal the inlet and outlet.

2. A device as disclosed in claim 1, wherein a gap between the windings and the rotor portion is defined by interposing walls of the pump unit and the motor unit.

3. A device as disclosed in claim 1, wherein the rotor comprises an impeller formed of a resiliently deformable material.

4. A device as disclosed in claim 1, wherein the rotor comprises an impeller rotatable at a speed where the impeller harmonically vibrates so as to form pulsating blood flow through the device.

5. A device as disclosed in claim 1, wherein the rotor comprises a shaft mounted between two rotor shaft bearings and one of the rotor shaft bearings is resiliently mounted within the pump unit so as to compensate for bearing wear.

6. A device as disclosed in claim 1, further comprising an inflow cannula, implantable in the left atrium attached to the inlet, and an outflow cannula, implantable in the aorta, attached to the outlet.

7. A device as disclosed in claim 6, further comprising permanently sealable shape memory metal valves disposed in the inflow cannula and the outflow cannula.

8. A device as disclosed in claim 1, wherein the rotor comprises an Archimedes screw.

9. An implantable cardiac assist device, comprising:

an outer housing;

a pump unit within the housing, having an inlet and outlet connectable to a patient's cardiovascular system and having a rotor portion therein rotatable to force blood entering the pump unit through the inlet out through the outlet, the rotor portion including an impeller formed of a resiliently deformable material; and a motor unit within the outer housing and hermetically sealed from the pump unit, the motor unit including control electronics and windings to produce a magnetic field couplable to the rotor portion, the motor unit being couplable to a power supply.

10. A device as disclosed in claim 9, wherein a gap between the windings and the rotor portion is defined by interposing walls of the pump unit and the motor unit.

11. A device as disclosed in claim 9, wherein the rotor comprises an impeller formed of a resiliently deformable material.

12. A device as disclosed in claim 9, wherein the rotor comprises an impeller rotatable at a speed where the impeller harmonically vibrates so as to form pulsating blood flow through the device.

13. A device as disclosed in claim 9, wherein the rotor comprises a shaft mounted between two rotor shaft bearings and one of the rotor shaft bearings is resiliently mounted within the pump unit so as to compensate for bearing wear.

14. A device as disclosed in claim 9, further comprising an inflow cannula, implantable in the left atrium attached to the inlet, and an outflow cannula, implantable in the aorta, attached to the outlet.

15. A device as disclosed in claim 14, further comprising permanently sealable shape memory metal valves disposed in the inflow cannula and the outflow cannula.

16. An implantable cardiac assist device, comprising:

an outer housing;

a pump unit within the housing, having an inlet and outlet connectable to a patient's cardiovascular system and having a rotor portion therein rotatable to force blood entering the pump unit through the inlet out through the outlet;

a motor unit within the outer housing and hermetically sealed from the pump unit, the motor unit including control electronics and windings to produce a magnetic field couplable to the rotor portion, the motor unit being couplable to a power supply;

an inflow cannula, implantable in the left atrium attached to the inlet, and an outflow cannula, implantable in the aorta: and permanently sealable shape memory metal valves disposed in the inflow cannula and the outflow cannula.

* * * * *